United States Patent [19]

Enders et al.

[11] 4,173,645

[45] Nov. 6, 1979

[54] SUBSTITUTED 4,5-DIHYDROXY-IMIDAZOLIDINE-2-THIONES AND THEIR USE AS ECTOPARASITICIDES

[75] Inventors: Edgar Enders, Cologne; Volker Ebbighausen, Leverkusen; Wolfgang Gau, Wuppertal; Christian Wünsche, Schwelm; Wilhelm Stendel, Wuppertal, all of Fed. Rep. of Germany

[73] Assignee: Bayer Aktiengesellschaft, Leverkusen, Fed. Rep. of Germany

[21] Appl. No.: 858,917

[22] Filed: Dec. 8, 1977

[30] Foreign Application Priority Data

Dec. 22, 1976 [DE] Fed. Rep. of Germany ....... 2658058
Jan. 20, 1977 [DE] Fed. Rep. of Germany ....... 2702236
Feb. 15, 1977 [DE] Fed. Rep. of Germany ....... 2706265

[51] Int. Cl.$^2$ .................... C07D 233/02; A01N 9/22
[52] U.S. Cl. ................................. 424/273 R; 548/319
[58] Field of Search ..................... 548/319; 424/273 R

[56] References Cited

U.S. PATENT DOCUMENTS

| 3,260,565 | 7/1966 | Beachem | 548/319 |
| 3,487,088 | 12/1969 | Remley | 548/319 |
| 3,905,996 | 9/1975 | Perronnet et al. | 548/319 |

FOREIGN PATENT DOCUMENTS

783051 9/1957 United Kingdom ..................... 548/319

Primary Examiner—Alan L. Rotman
Attorney, Agent, or Firm—Sprung, Felfe, Horn, Lynch & Kramer

[57] ABSTRACT

The present invention provides, as compounds, the substituted 4,5-dihydroxy-imidazolidine-2-thiones of the general formula

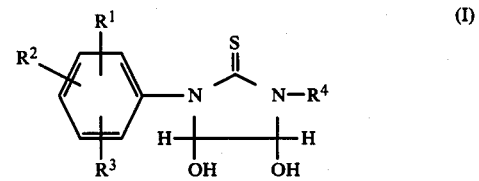

in which $R^1$, $R^2$ and $R^3$, which are selected independently of one another each represent hydrogen, optionally substituted alkyl, optionally substituted alkoxy or halogen and $R^4$ represents optionally substituted alkyl, cycloalkyl or alkenyl.

It has been found that the compounds of this invention have a powerful ectoparasiticidal action, in particular against acarids.

6 Claims, No Drawings

SUBSTITUTED 4,5-DIHYDROXY-IMIDAZOLIDINE-2-THIONES AND THEIR USE AS ECTOPARASITICIDES

The present invention relates to certain substituted 4,5-dihydroxy-imidazolidine-2-thiones, to a process for their preparation and to their use as ectoparasiticides.

The present invention provides, as compounds, the substituted 4,5-dihydroxy-imidazoline-2-thiones of the general formula

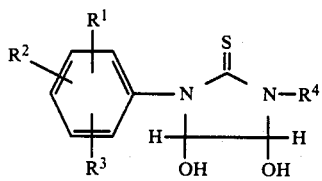

in which $R^1$, $R^2$ and $R^3$, which are selected independently of one another each represent hydrogen, optionally substituted alkyl, optionally substituted alkoxy or halogen and $R^4$ represents optionally substituted alkyl, cycloalkyl or alkenyl.

It has been found that the compounds of this invention have a powerful ectoparasiticidal action, in particular against acarids.

Preferably, $R^1$, $R^2$ and $R^3$, which are selected independently of one another, each represent hydrogen, alkyl with 1-6 (especially 1-4) carbon atoms (for example, methyl, ethyl, n- or iso-propyl or n-, iso-, sec.- or tert.-butyl), halogenoalkyl with 1-4 (especially 1 or 2) carbon atoms and 1-5 (especially 1-3) halogen atoms selected independently of one another (preferred halogens being chlorine and fluorine, as in, for example, trifluoromethyl, chlorodifluoromethyl, 2,2,2-trifluoroethyl and pentafluoroethyl), alkoxy with 1-6 (especially 1-4) carbon atoms (for example, methoxy, ethoxy, n- or isopropoxy or n-, iso- or tert.-butoxy), chlorine, bromine or -fluorine, and $R^4$ represents alkyl with 1-6 (especially 1-4) carbon atoms or monocyclic, bicyclic or tricyclic cycloalkyl with 3-10 (especially 3, 5 or 6) carbon atoms (for example cyclopropyl, cyclobutyl, cyclopentyl, cyclohexyl, cycloheptyl, bicyclo[2.2.1]heptyl, bicyclo[2.2.2]octyl or adamantyl), cycloalkyl-alkyl or cycloalkenyl such as cyclopropylmethyl, cyclohexylmethyl, cyclopentenyl or cyclohexenyl.

It is to be understood that the alkyl radicals $R^1$, $R^2$, $R^3$ and $R^4$ and the alkoxy radicals $R^1$, $R^2$ and $R^3$ may be optionally substituted. Preferred substituents are halogen, halogenoalkyl, and halogenoalkoxy especially chlorine, fluorine, bromine, trifluoromethyl, trifluoroethyl and trifluoromethoxy.

Particularly preferred compounds are those of the formula (I) in which $R^1$ and $R^2$, which can be identical or different, each represent hydrogen, $C_1-C_4$ alkyl, trifluoromethyl or chlorine, $R^3$ represents hydrogen and $R^4$ represents $C_1-C_4$ alkyl, and their salts.

The present invention also provides a process for the preparation of a substituted 4,5-dihydroxy-imidazolidine-2-thione of the formula (I), in which a substituted thiourea of the general formula

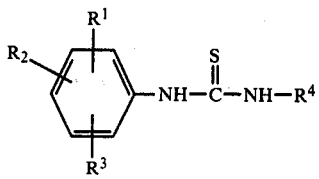

in which $R^1$, $R^2$, $R^3$ and $R^4$ have the meanings stated above, is reacted with glyoxal, optionally in the presence of an acid or a base, in an inert organic solvent.

Instead of glyoxal, it is also possible to employ compounds which are converted into glyoxal under the reaction conditions, such as acetals or hemi-acetals of glyoxal or glyoxal-sodium bisulphite adducts.

If N-(2,4-dimethyl-phenyl)-N'-methyl-thiourea and glyoxal are used as starting materials, the course of the reaction can be illustrated by the following equation:

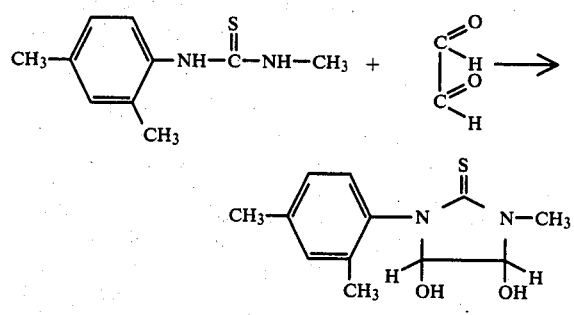

The reaction of compounds of the formula (II) with glyoxal to give the compounds of the formula (I) represents a new and surprisingly elegant path to the class of 4,5-dihydroxy-imidazolidine-2-thiones. It was not to be expected that this reaction could proceed in such a simple manner and with high yields, that is to say without the formation of relatively large amounts of by-products.

The compounds of the formula (II) employed as starting materials are known or can be prepared in a simple manner by known methods, either by reacting substituted phenylisothiocyanates of the general formula (III) with aliphatic amines of the general formula (IV)

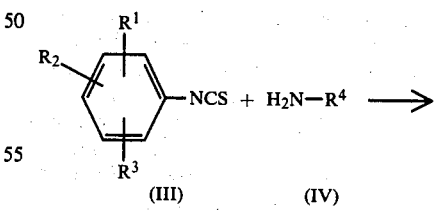

or by reacting substituted phenylamines of the general formula (V) with alkylisothiocyanates or alkenylisothiocyanates of the general formula (VI)

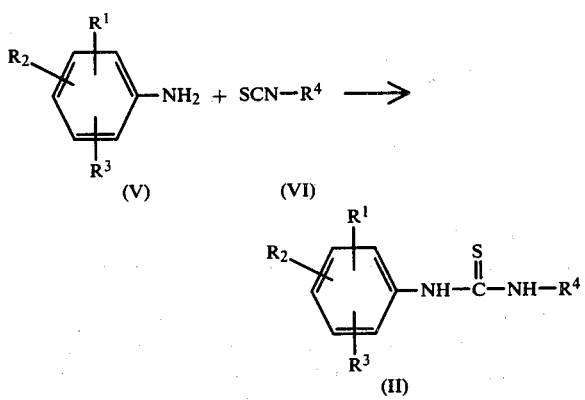

the radicals R¹, R², R³ and R⁴ in formulae (III), (IV), (V), (VI) and (II) having the meanings stated above.

Examples of substituted phenylthioureas of the formula (II) which are employed, according to the invention, as starting materials are: N-(2,4-dimethylphenyl)-N'-methyl-thiourea, N-(2,4-dimethyl-phenyl)-N'-ethyl-thiourea, N-(2,4-dimethyl-phenyl)-N'-propyl-thiourea, N-(2,4-dimethyl-phenyl)-N'-isopropyl-thiourea, N-(2,4-dimethyl-phenyl)-N'-allyl-thiourea, N-(2,4-dimethyl-phenyl)-N'-methallyl-thiourea, N-(2,4-dimethyl-phenyl)-N'-crotyl-thiourea, N-(2,4-dimethyl-phenyl)-N'-cyclopropyl-thiourea, N-(2,4-dimethyl-phenyl)-N'-butyl-thiourea, N-(2,4-dimethyl-phenyl)-N'-tert.-butyl-thiourea, N-(2-methyl-4-ethyl-phenyl)-N'-methyl-thiourea, N-(2-methyl-4-ethyl-phenyl)-N'-ethyl-thiourea, N-(2-methyl-4-ethyl-phenyl)-N'-allyl-thiourea, N-(2-ethyl-4-methyl-phenyl)-N'-methyl-thiourea, N-(2-ethyl-4-methyl-phenyl)-N'-ethyl-thiourea, N-(2,4,5-trimethyl-phenyl)-N'-methyl-thiourea, N-(2,4,5-trimethyl-phenyl)-N'-ethyl-thiourea, N-(2,4,5-trimethyl-phenyl)-N'-allyl-thiourea, N-(2,4,5-trimethyl-phenyl)-N'-cyclopropyl-thiourea, N-(2,3,4-trimethyl-phenyl)-N'-methyl-thiourea, N-(2,3,4-trimethyl-phenyl)-N'-ethyl-thiourea, N-(2,3,4-trimethyl-phenyl)-N'-methallyl-thiourea, N-(2,4,6-trimethyl-phenyl)-N'-methyl-thiourea, N-(3-methyl-2,4-diethyl-phenyl)-N'-methyl-thiourea, N-(5-methyl-2,4-diethylphenyl)-N'-methyl-thiourea, N-(5-chloro-2,4-dimethyl-phenyl)-N'-methyl-thiourea, N-(3,5-bis-trifluoromethyl-phenyl)-N'-methyl-thiourea and N-(3,4-dichloro-phenyl)-N'-methyl-thiourea.

Examples of the compounds of the formula (V) which may be employed in the preparation of the compounds of the formula (II) are: 2,4-dimethylaniline, 2-methyl-4-ethylaniline, 2-methyl-4-propylaniline, 2-methyl-4-butyl-aniline, 2-methyl-4-isopropyl-aniline, 2-methyl-4-isobutyl-aniline, 2-methyl-4-sec.-butyl-aniline, 2-methyl-4-tert.-butyl-aniline, 2-ethyl-4-methyl-aniline, 2,4-diethylaniline, 2-ethyl-4-isopropylaniline, 2-ethyl-4-tert.-butyl-aniline, 2,4-diisopropyl-aniline, 2,4-di-sec.-butyl-aniline, 2,4-ditert.-butylaniline, 2,4,5-trimethyl-aniline, 2,3,4-trimethyl-aniline, 2,4,6-trimethyl-aniline, 3-methyl-2,4-diethylaniline, 5-methyl-2,4-diethylaniline, 5-chloro-2,4-dimethyl-aniline, 5-bromo-2,4-dimethyl-aniline, 5-fluoro-2,4-dimethyl-aniline, 2,5-dimethyl-4-chloro-aniline, 2-ethyl-3,4-dimethyl-aniline, 2,6-dimethyl-aniline, 2,6-diethyl-aniline, 2,6-disec.-butyl-aniline, 3,4-dichloroaniline, 3,4-dimethoxy-aniline and 3,5-bis-trifluoromethyl-aniline.

Examples of alkyl-amines and alkenyl-amines of the general formula (IV) are: methylamine, ethylamine, propylamine, isopropylamine, butylamine, sec.-butylamine, isobutylamine, tert.-butylamine, allylamine, methallylamine, crotylamine and cyclopropylamine.

Examples of substituted phenylisothiocyanates of the general formula III are: (2,4-dimethylphenyl)-isothiocyanate, (2,4-dimethylphenyl)-isothiocyanate, (2,4-dimethylphenyl)-isothiocyanate, (2,4-dimethylphenyl)-isothiocyanate, (2,4-dimethylphenyl)-isothiocyanate, (2,4-dimethylphenyl)-isothiocyanate, (2,4-dimethylphenyl)-isothiocyanate, (2,4-dimethylphenyl)isothiocyanate, (2,4-dimethylphenyl)-isothiocyanate, (2,4-dimethylphenyl)-isothiocyanate, (2-methyl-4-ethyl-phenyl)-isothiocyanate, (2-methyl-4-ethyl-phenyl)-isothiocyanate, (2-methyl-4-ethyl-phenyl)-isothiocyanate, (2ethyl-4-methyl-phenyl)-isothiocyanate, (2-ethyl-4-methyl-phenyl)-isothiocyanate, (2,4,5-trimethyl-phenyl)-isothiocyanate, (2,4,5-trimethyl-phenyl)-isothiocyanate, (2,4,5-trimethyl-phenyl)-isothiocyanate, (2,4,5-trimethyl-phenyl)-isothiocyanate), (2,3,4-trimethyl-phenyl)-isothiocyanate, (2,3,4-trimethyl-phenyl)-isothiocyanate, (2,3,4-trimethyl-phenyl)-isothiocyanate, (2,4,6-trimethyl-phenyl)-isothiocyanate, (3-methyl-2,4-diethyl-phenyl)-isothiocyanate, (5-methyl-2,4-diethyl-phenyl)-isothiocyanate, (5-chloro-2,4-dimethyl-phenyl)-isothiocyanate, (3,5-bis-trifluoromethyl-phenyl)-isothiocyanate and (3,4-dichloro-phenyl)-isothiocyanate.

Examples of isothiocyanates of formula VI are: methylisothiocyanate, ethylisocyanate, propylisothiocyanate, isopropylisothiocyanate, butylisothiocyanate, sec. butylisothiocyanate, isobutylisothiocyanate, tert.-butylisothiocyanate, allylisothiocyanate, methallylisothiocyanate, crotylisothiocyanate and cyclopropylisothiocyanate.

In general, equimolar amounts may be used for the reaction of the compounds of the formula (II) with glyoxal, but a small excess of glyoxal, for example about 5-30 mole percent, is preferred. Possible inert solvents are those which are capable of dissolving, or at least partially dissolving, the thiourea derivative of the formula (II) used as the starting material. Examples of solvents which may be mentioned are: alcohols, such as alkanols having 1 to 4 carbon atoms, for example, methanol, ethanol, isopropanol, sec.-butanol and alkanediols having 2 to 3 carbon atoms, ethylene glycol; ketones, such as acetone, butanone, methyl ethyl ketone and methyl isopropyl ketone; ethers, such as 1,2-dimethoxyethane, diethyl ether, diisopropyl ether, tetrahydrofuran and dioxan; carboxylic acid derivatives, such as acetonitrile, ethyl acetate, dimethylformamide, diethylformamide, dimethylacetamide and N-methylpyrrolidone; and hydrocarbons and chlorohydrocarbons, such as chlorinated alkanes, for example, methylene chloride, chloroform, carbon tetrachloride; alkanes and cycloalkanes, for example, n-hexane, cyclohexane and monocyclic carbocyclic hydrocarbons, for example, benzene or toluene.

Water and acids or bases having a catalytic action can be added to the reaction batches, for example p-toluenesulphonic acid, sodium hydrogen sulphate, phosphoric acid, oxalic acid or acetic acid, or bases, such as sodium hydroxide, potassium hydroxide, trisodium phosphate, potassium acetate, trimethylamine, triethylamine, diisopropylamine, and potassium tert.-butylate. The temperature conditions for the reaction according to the invention can vary within wide limits. When the solvent is suitably chosen, the reaction proceeds exothermically and can be easily controlled by cooling or regulating the addition of the reagents. In general, the reaction is carried out at from about 20° C. to 150° C., preferably at from about 20° to 80° C.

In general, the reaction product of the formula (I) formed is worked up either by precipitating the reaction product with water or by distilling off the organic solvent, subsequently washing the residue with water and recrystallising the reaction product of the formula (I) in a manner which is in itself known.

The compounds of the formula (I) exhibit powerful acaricidal properties, especially against acarids which, as animal ectoparasites, attack domestic animals such as cattle, sheep and rabbits. Moreover, the 4,5-dihydroxy-imidazolidine-2-thiones have only a low toxicity towards warm-blooded animals. They are therefore very suitable for combating animal ectoparasites from the class of the acarids. In addition, however, they also possess an action against other acarids and against insects.

As examples there may be mentioned scab mites, lice and Diptera as well as their larvae.

As economically important ectoparasites which play a major roll especially in tropical and sub-tropical countries there may be mentioned the Australian and South American cattle tick *Boophilus microplus*, the South African cattle tick *Boophilus decoloratus*, both from the family of the Ixodidae, and the cattle and sheep ticks.

In the course of time, ticks, in particular, have become resistant to the phosphoric acid esters and carbamates hitherto used as combating agents, so that the success of combating them has in many areas become increasingly dubious. To ensure economical stock raising in the infected areas there is an urgent need for agents by means of which all stages of development, that is to say larvae, nymphs, metanymphs and adults, even of resistant strains, for example of the genus Boophilus, can be combated reliably. For example, in Australia the Mackay strain, the Biarra strain and the Mount Alford strain of *Boophilus microplus* are highly resistant to the phosphoric acid esters hitherto used.

The active compounds according to the invention are equally effective both against the normally sensitive strains and against the resistant strains, for example of Boophilus. When applied in the usual manner to the host animal, they act both directly against all forms parasitic on the animal and strongly ovicidally on the adult forms, so that the reproductive cycle of the ticks is interrupted both in the parasitic phase on the animals and in the non-parasitic phase. The laying of eggs is prevented and the development and slipping is inhibited. Aspects to be singled out particularly are the rapidly manifested excitation effect on all parasitic forms, which release their suction hold, migrate in a non-physiological manner on the host animal, drop off and finally die (detaching effect) and in particular also the good action against the metanymph stages which experience has shown to be difficult to combat.

Furthermore, they act in the same manner against all stages of development of multi-host ticks, such as, for example, Amblyomma spp., Hyalomma spp., Rhipicephalus spp., Ixodes spp., *Mama physalis* spp. and Dermacentor spp.

A detaching effect is also shown in the case of insects, for example lice, such as Haematopimis spp.

The active compounds can be converted into the customary formulations, such as solutions, emulsions, suspensions, powders, pastes and granules.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkylnaphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The formulations in general contain from 0.1 to 95 percent by weight of active compound, preferably from 0.5 to 90 percent by weight.

The ready-to-use preparations are generally prepared from the concentrated formulations by dilution with water. The concentrations can, depending on the manner of use, be varied within a wide range; in general they are from 10 to 50,000 ppm (g/g), preferably from 50 to 500 ppm.

Application is effected in the usual manner, for example by spraying, pouring, atomising or the use of a bath or dip.

Other auxiliaries or active compounds, such as disinfectants or specifically suitable insecticides, can also be admixed to the formulations or to the ready-to-use solutions.

The aqueous solutions or emulsions of the active compounds according to the invention are very stable under practical conditions, so that the ready-to-use forms for application remain active even on prolonged standing and in a pH range of 7–9 for three months or more.

The present invention also provides an ectoparasiticidal composition containing as active ingredient a compound of the present invention in admixture with a solid or liquefied gaseous diluent or carrier or in admixture with a liquid diluent or carrier containing a surface-active agent.

The present invention also provides a method of freeing or protecting domesticated animals from ectoparasitical acarids or insects which comprises externally applying to said animals a compound according to the present invention, preferably in admixture with a diluent or carrier.

The present invention further provides domesticated animals whenever freed or protected from ectoparasitical acarids or insects by the external application to said animals of a compound according to the present invention, in admixture with a diluent or carrier.

The ectoparasiticidal activity of the compounds of this invention is illustrated by the following biotest Example.

EXAMPLE A

Test with adult cattle ticks (*Boophilus microplus* resistant)

Solvent: Cremophor

To produce a suitable preparation of active compound, the active substance in question was mixed with the stated solvent in the ratio of 1:2 and the concentrate thus obtained was diluted with water to the desired concentration.

10 adult cattle ticks (*B. microplus,* Biarra strain, res.) were dipped for 1 minute into the active compound preparation to be tested. After transfer into plastic cups and storage in a climatically controlled room, the degree of destruction in percent was determined, 100% meaning that all of the ticks had been killed.

The results are shown in the following table.

Table A

| Active compound | Active compound concentration in ppm | Destructive action in % |
|---|---|---|
| (structure A) | 10,000 | 100 |
| | 3,000 | 100 |
| | 1,000 | >50 |

(A): 1-(2,4-dimethylphenyl)-3-methyl-4,5-dihydroxy-imidazolidine-2-thione structure The process of the present invention is illustrated by the following preparative Examples.

EXAMPLE 1

1-(2,4-Dimethyl-phenyl)-3-methyl-4,5-dihydroxy-imidazolidine-2-thione 30.0 g of N-(2,4-dimethylphenyl)-N'-methyl-thiourea were stirred with 150 ml of 1,2-dimethoxy-ethane and 10 ml of triethylamine, and 36.0 g of a 30% strength aqueous solution of glyoxal was added. After stirring for a short time, the thiourea slowly dissolved, the reaction being exothermic. The temperature was allowed to rise to 50° C. and the solution was kept at this temperature for a further 1 hour. Thereafter, the solvent was distilled off in vacuo and the oily residue was stirred with water, with the addition of a little acetic acid. The reaction product, which solidified in the crystalline form, was filtered off, washed with water and dried. The yield was 37 g. For purification, the product could be recrystallised from isopropyl alcohol.

Melting point: 156°–157° C., with decomposition.

The elementary analysis and the H-NMR, C-13-NMR and IR spectra were in agreement with the supposed structure.

EXAMPLE 2

1-(2-Ethyl-phenyl)-3-methyl-4,5-dihydroxy-imidazolidine-2-thione 30.0 g of N-(2-ethyl-phenyl)-N'-methyl-thiourea were stirred in 200 ml of dimethoxyethane and 10 ml of triethylamine, and 36.0 g of a 30% strength aqueous glyoxal solution were added. The mixture was stirred for 1 hour at 20° C. and for 1 hour at 50° C., the thiourea dissolving completely. The solvent was distilled off in vacuo, the residue was stirred with water and a little dilute acetic acid and the oily reaction product was taken up in methylene chloride. The methylene chloride solution was washed with water, dried over potassium carbonate, concentrated and completely freed from the solvent at 60°/1.0 mm Hg. This gave 26.0 g of the reaction product as a viscous oil which slowly solidified. The elementary analysis and the NMR spectra were in agreement with the supposed structure.

Analogously to Example 2, N-(2,6-diethyl-phenyl)-N'-methyl-thiourea gave 1-(2,6-diethyl-phenyl)-3-methyl-4,5-dihydroxy-imidazolidine-2-thione (melting point: 87°–90° C.); N-(2,6-dimethylphenyl)-N'-methyl-thiourea gave 1-(2,6-dimethyl-phenyl)-3-methyl-4,5-dihydroxy-imidazolidine-2-thione (melting point: 140°–143° C.); N-(3,5-dichlorophenyl)-N'-methyl-thiourea gave 1-(3,5-dichloro-phenyl)-3-methyl-4,5-dihydroxy-imidazolidine-2-thione (melting point: 143° C.); and N-(2,4,5-trimethyl-phenyl)-N'-methyl-thiourea gave 1-(2,4,5-trimethyl-phenyl)-3-methyl-4,5-dihydroxy-imidazolidine-2-thione.

EXAMPLE 3

1-(3,5-bis-Trifluoromethyl-phenyl)-3-methyl-4,5-dihydroxy-imidazolidine-2-thione 30.0 g of N-(3,5-bis-trifluoromethyl-phenyl)-N'-methyl-thiourea were stirred in 100 ml of 1,2-dimethoxyethane and 10 ml of triethylamine, and then 22 g of a 30% strength aqueous glyoxal solution were added. The thiourea thereupon dissolved, the reaction being exothermic. The solution was stirred for a further 12 hours at 20° C. and was concentrated in vacuo and the residue was stirred with water and a little acetic acid. The reaction product, which had solidified, was filtered off, washed and dried. Yield 32.0 g; melting point: 133°–135° C. after recrystallisation from toluene.

The elementary analysis and the H-NMR and C-13-NMR spectra were in agreement with the supposed structure.

Analogously, N-(3,4-dichlorophenyl)-N'-methyl-thiourea gave 1-(3,4-dichlorophenyl)-3-methyl-4,5-dihydroxy-imidazolidine-2-thione (melting point: 115°–117° C.).

The compounds according to the invention can also be used in combination with further ectoparasiticidal, and in particular tickicidal, active compounds. Thus, virtually all the commercially available ectoparasiticidal active compounds, and also other ectoparasiticidal active compounds, can be employed in combination with the active compounds according to the invention.

The active compounds (thiazoline derivatives) known from German Offenlegungsschrift (German Published Specification) No. 2,619,724 are particularly suitable for combination.

For example, the following combination can be employed:

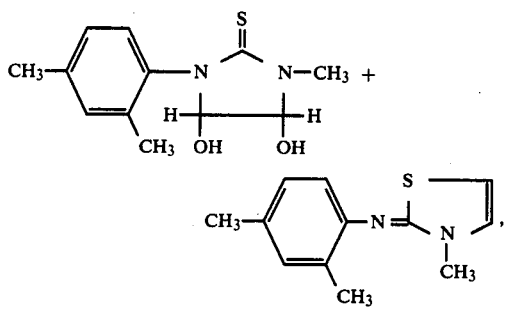

it being possible for the ratio of parts by weight of (A) to parts by weight of (B) in the formulation to vary greatly; in practice, an excess of component (B) is preferably present. A ratio range which can be indicated as preferred is: 5 to 50 parts by weight of (A) to 50 to 95 parts by weight of (B). The total concentrations, (A)+(B), in the formulations can be varied within a substantial range, depending on the use form. A preferred range is the concentration range between 10 and 500 ppm. The above-mentioned combination (A)+(B) is particularly suitable for animal dip formulations.

What is claimed is:

1. A compound accord of the formula

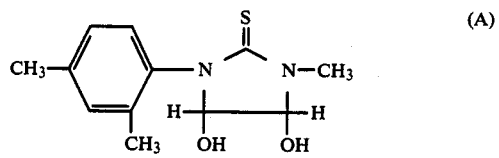

2. An ectoparasiticidal composition containing as active ingredient an effective amount of a compound according to claim 1 in admixture with a solid or liquefied gaseous diluent or carrier or in admixture with a liquid diluent or carrier containing a surface-active agent.

3. A composition according to claim 2 containing from 0.1 to 95% of the active compound, by weight.

4. A method of freeing or protecting domesticated animals from ectoparasitical insects or acarids which comprises externally applying to said animals a compound according to claim 1, in admixture with a diluent or carrier.

5. A method according to claim 4 in which a composition is used containing from 10 to 50,000 ppm of the active compound, by weight.

6. A method according to claim 5 in which a composition is used containing from 50 to 500 ppm of the active compound, by weight.

* * * * *